United States Patent [19]

Levin et al.

[11] 4,191,950
[45] Mar. 4, 1980

[54] ANTI-BED-WETTING DEVICE

[76] Inventors: Paul D. Levin; Anne F. Levin, both of 1595 Soquel Dr., Santa Cruz, Calif. 95065

[21] Appl. No.: 920,066

[22] Filed: Jun. 28, 1978

Related U.S. Application Data

[63] Continuation-in-part of Ser. No. 876,221, Feb. 9, 1978, abandoned.

[51] Int. Cl.² .............................................. G08B 21/00
[52] U.S. Cl. ................................. 340/604; 128/138 A; 340/384 E
[58] Field of Search ................. 340/602, 604; 361/223, 361/224; 128/138, 138 A, DIG. 4, DIG. 15, 291, 2.06 E, 2.1 E

[56] References Cited

U.S. PATENT DOCUMENTS

| | | | |
|---|---|---|---|
| 2,355,752 | 8/1944 | Repking | 340/642 |
| 2,874,695 | 2/1959 | Vaniman | 128/138 A |
| 3,199,095 | 8/1965 | Ashida | 340/602 |
| 3,460,123 | 8/1969 | Bass | 340/604 |
| 3,490,442 | 1/1970 | Streu | 128/2.06 E |
| 3,530,855 | 9/1970 | Balding | 340/604 |
| 3,542,010 | 11/1970 | Love | 128/2.1 E |
| 3,592,195 | 7/1971 | Van Wagenen | 340/604 |
| 3,809,078 | 5/1974 | Mozes | 128/138 A |
| 3,954,100 | 5/1976 | Sem-Jacobsen | 128/2.06 E |
| 4,072,145 | 2/1978 | Silva | 128/2.1 E |

Primary Examiner—John W. Caldwell, Sr.
Assistant Examiner—Daniel Myer
Attorney, Agent, or Firm—Robert G. Slick

[57] ABSTRACT

An improved moisture-sensing device, preferably combined with an improved lead, is provided which represents a significant advance in the state of the art in the treatment of enuretic children. Both sensor and lead utilize a special type of conductive polyvinyl cloth and the components are connected by silver-impregnated Velcro ®.

2 Claims, 18 Drawing Figures

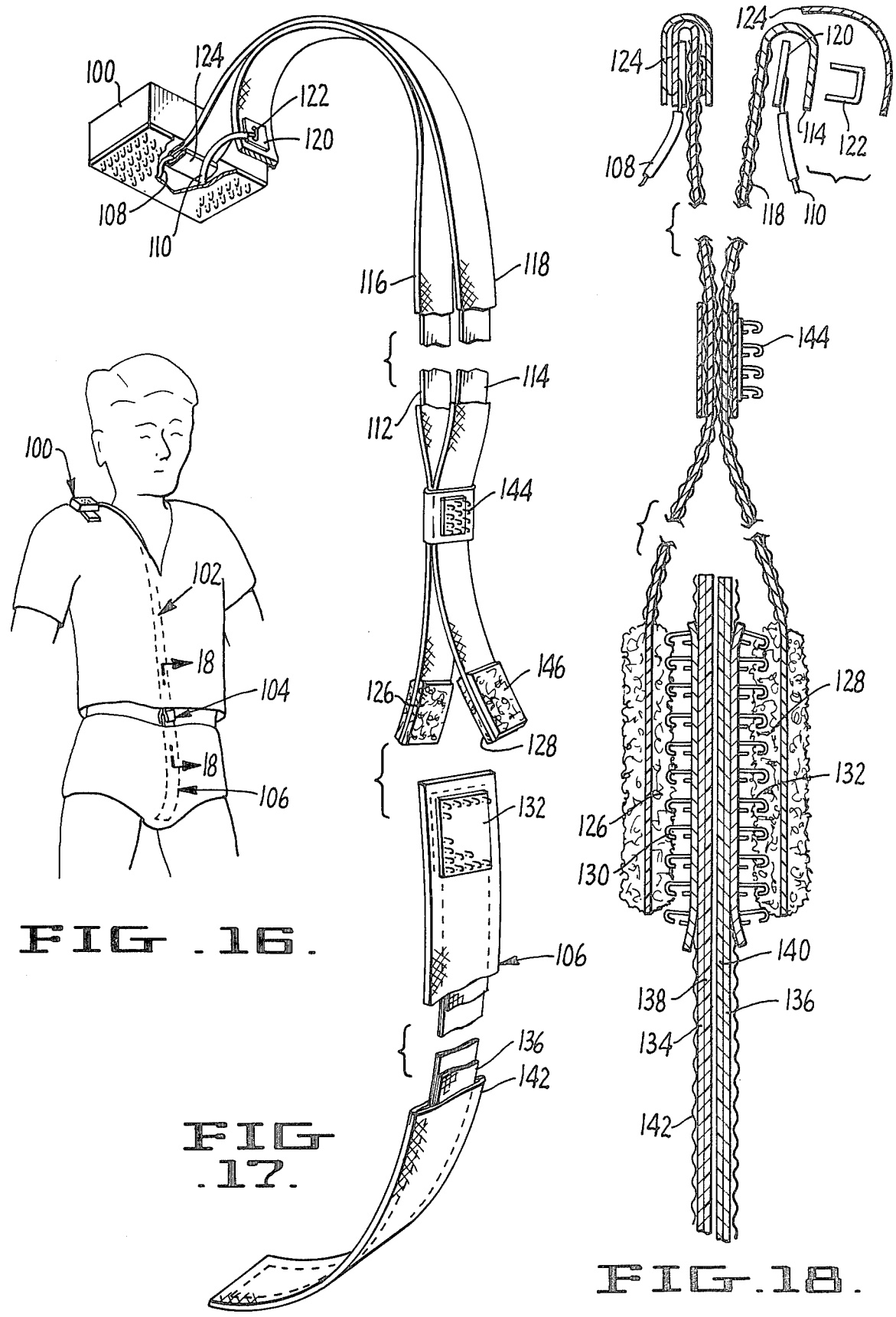

ANTI-BED-WETTING DEVICE

REFERENCE TO RELATED APPLICATION

This application is a continuation-in-part of our application Ser. No. 876,221, filed Feb. 9, 1978, now abandoned.

SUMMARY OF THE INVENTION

Various anti-bed-wetting devices have been used in the past to train enuretic children to get up in time to empty their bladders and avoid bed-wetting. The first such devices consisted of metallic grids placed under the bedsheet and separated by absorbent but nonconductive material such as cotton cloth. The flow of urine into the bed would activate a bedside alarm shortly after urination by virtue of a circuit being closed and previously nonconducting dry cloth would become conductive when wet by electrolyte-containing urine. These devices have the disadvantage of a moderate delay of between 5 and 10 seconds before the alarm would sound after the onset of urination. There was also the inconvenience necessitated by changes of bed linen during the night.

In the past several years different devices have been proposed which are portable and which are activated by urine in the area of the child's perineum or underwear or sleepwear, thereby decreasing the time between the onset of urination and the triggering of the alarm and with the additional advantage of at least theoretically reducing the amount of urine flowing into the bed.

The present invention does not claim originality in regard to portability of the device, but does claim to a significant improvement in the state of the art because of the type of sensor employed and, in a preferred embodiment, because of the means of making the electrical connection between the sensor and the alarm, the latter to be worn on the shoulder of the sleeping child.

Previous devices have been less than completely acceptable to many children because of the bulkiness of the device in the area of the perineum or the long length of rather stiff electrical cord which necessarily had to reach from the area of the alarm (such as on the wrist, up the arm, and down to the perineal area). An additional disadvantage of previous devices is that the sensor is rather small, covering a very limited area and may be missed by the flow of urine, particularly in boys. If the flow of urine does not hit the metallic buttonlike sensor in such a device, the alarm may not be activated at all and the entire urine flow may be directed into the underlying bed without triggering the alarm. This event has, in fact, been found to occur using this particular type of sensing mechanism.

In the present invention to be described, a significant improvement in the state of the art, the sensor consists of a long double strip of conductive vinyl cloth surrounded by a soft cotton flannel tube which is fastened easily to a pair of ordinary undershorts and is connected via special silverimpregnated Velcro ® fasteners to a conductive material leading up to the alarm device which is placed in the shoulder region of the child. The polyvinyl cloth strips are readily incorporated into a cotton-covered tube to make a sensor which covers a wide area over the perineum. Such a sensor is soft to the touch and flexible. It can be repeatedly laundered with the underpants to which it is permanently attached by stitching or, more conveniently, iron-on tape.

We claim advantages of this particular system for the following reasons:

1. The arrangement is more comfortable than previous devices because of the use of a soft ribbon-like conductor made of cloth which is not noticed by the child in contrast to a stiff wire conductor and therefore makes the device more acceptable and likely to be used by the enuretic child.

2. The sensor to be described covers a fairly wide area of the perineum and is wet easily by urine which is directed either to the right, forward, or to the left, thereby virtually always triggering the onset of urination.

3. Since the sensor device is always in place on the child's undershorts, the child must make no particular effort to place a special button sensor in exactly the right area. In addition, the difficulty of placing a double snap over thick underwear or pajamas is also avoided, a particular difficulty with small children.

4. The use of conductive Velcro ® in this instance complements the entire system and can be readily sewn to the conductive vinyl cloth. The Velcro ® connect-/disconnect system is easy to use by a child of any age and provides a realiable and inexpensive "plug and jack" method of connecting the upper and lower halves of the system.

The essence of this invention is the use of a special polyvinyl cloth as a substitute for metallic conductors in at least the sensor and preferably both the sensor and the long lead from the electronic device and alarm which is to be located on the shoulder of the child. The use of the conductive cloth facilitates the use of Velcro ® as a connecting device between the upper and lower parts of the system. A particular type of Velcro ® is utilized in which the nylon is impregnated with silver.

The preferred lead from the shoulder region consists of two thin strips of conductive cloth, each about ⅜ inch wide, which are each enclosed inside separate flat tubes of dacron, thereby insulating the conductive polyvinyl cloth and also giving a smooth, soft surface to the lead which is comfortable to the touch.

The upper end of the lead must terminate in an ordinary conductive wire so that such a wire can then be soldered to the proper terminal of the electronic alarm device. This is accomplished at the upper end of the lead by simply folding the polyvinyl strip over a small piece of conductive rubber. A staple then perforates the polyvinyl cloth, the conductive rubber, and the dacron, thereby crimping the wire and rubber very tightly to the polyvinyl cloth. The other end of the wire lead is soldered into the circuit board of the alarm device. At the lower end of the lead, staples are the most convenient method to fasten a small square of conductive Velcro ® to a protruding portion of the conductive vinyl strip. A second staple is used to strengthen the attachment of the Velcro ® to the dacron tube. Finally, to cover the major portion of the staples and to provide additional strength and improve the appearance, a square of ordinary Velcro ® but with a sticky back (furnished as "Scotchmate" by 3M Company) is placed over the backside of the conductive Velcro ®.

The method described gives a very strong method of attachment which is reliably conductive and of a pleasing appearance. An additional advantage of using ordinary Velcro ® on the back of the conductive Velcro ®

(both are of the nap type) is that one of the pairs of leads can be folded back, as illustrated in the drawings, and fastened to a small piece of hooked Velcro ® to prevent inadvertent sounding of the alarm.

The sensor strip, which is easily fastened to ordinary underwear by either sewing or with cross strips of iron-on tape, also utilizes conductive polyvinyl cloth. Again, the same advantages accrue with this technique since the cloth is soft and flexible and can be used in conjunction with conductive Velcro ® to mate with the leads previously described. Two strips of conductive cloth are employed and advantage is taken of the fact that the cloth as it comes from the manufacturer (Herculite Company) is conductive on only one side and with excellent insulation on the opposite side. Thus, it is possible to provide a very simple sensor wherein two strips of conductive cloth are employed with the nonconductive surfaces in contact with each other. These are enclosed in a simple cotton envelope of very absorbent flannel material. At the upper end of the sensor, provision is made for the attachment of two small squares of conductive Velcro ®, which are placed on opposite sides of the sensor. Having the Velcro ® squares on opposite sides rather than side-by-side prevents inadvertent touching of the leads and thereby avoids the child inadvertently sounding the alarm as the leads are attached to the sensor. The unit is very sensitive to moisture since a conductive path is established between the two polyvinyl strips whenever a small area of the edge of the sensor becomes moist from urine.

BRIEF DESCRIPTION OF THE DRAWINGS

FIG. 16 is a perspective view of a child wearing a preferred embodiment of the device wherein both the sensor and the connectors are formed of a conductive polyvinyl cloth.

FIG. 17 is an enlarged exploded view of the device shown in FIG. 16.

FIG. 18 is an enlarged section on the line 18—18 of FIG. 16.

DESCRIPTION OF THE PREFERRED EMBODIMENTS

Figure 1:
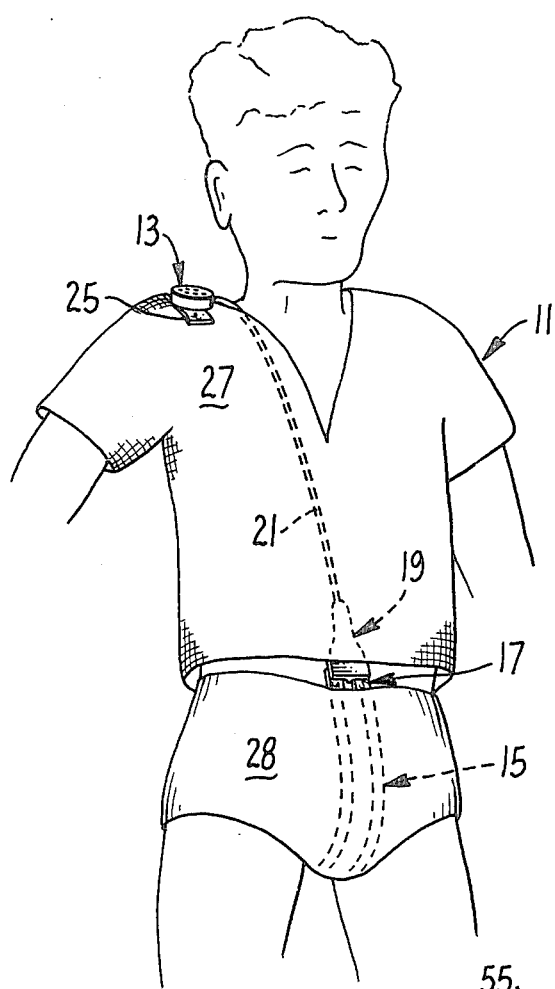
FIG. 1 is a perspective view of a child wearing a device embodying the sensor of the present invention.

Referring now to the drawings by reference characters, a child 11 is wearing a device of the present invention. The device consists of two main parts, namely, an alarm or sounder box 13 and a sensor 15. Sensor 15 is connected to a jack generally designated 17 to a plug 19 connected by suitable wires 21 to the alarm device 13.

The alarm box 13 has means for attachment to the upper garment. Preferably, this consists of a patch of Velcro ® 23 which mates with a patch of Velcro ® 25 which is attached to the upper garment 27 of the wearer. Although hook Velcro ® is shown for the pad 23 and loop for the pad 25, this relationship is not critical and can be reversed. The pad 25 is attached to the garment 27 by any suitable means such as sewing or preferably, by a heat-activated iron-on adhesive. The sensor forms part of, or is attached to, the lower portion 28 of the sleeping garment as is hereafter described.

The jack 17 and 19 and plug can be of the conventional type used for electrical connectors, but it is preferably made of conductive (silver-impregnated) Velcro ® since this results in minimum bulk and is easy for a child to work. This consists of two pads 29 of hook Velcro ® fastened to a nonconductive pad 31 which is attached to the upper garment 27 and to the mating loop pads 33 attached to the sensor 15. Obviously, the hook and loop relationship could be reversed.

As was previously mentioned, the sensor 15 is of a flexible material which is preferably fastened, by suitable means, to the lower portion 28 of the sleeping garment.

Figure 2:
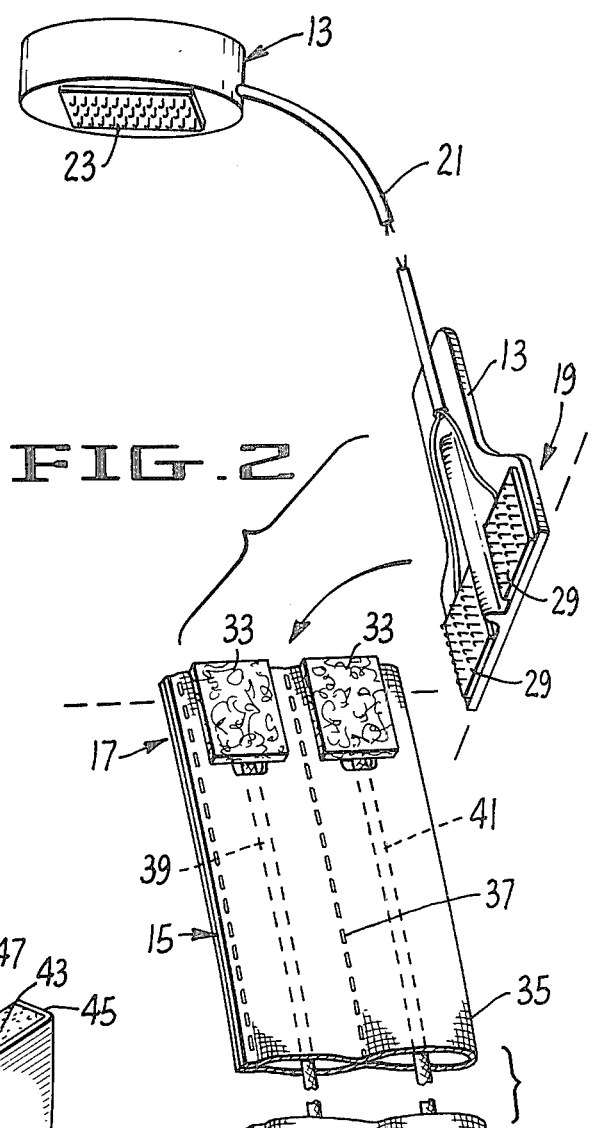
FIG. 2 is a perspective exploded view of a device embodying the present invention with some of the parts in section.

In the embodiment illustrated in FIG. 2, the sensor includes a double pouch of a diaper material 35 having a center seam 37. Wires 39 and 41 extend into the two compartments thus formed. The wires 39 and 41 are thin and flexible and preferably of stranded material and are ordinarily made of an inert metal such as stainless steel, silver or bronze. The wires 39 and 41 are attached to the Velcro ® pads 33 as previously described. The sensor unit can be sewn into the lower portion of the garment or can be attached by other suitable means such as a heat activated iron-on adhesive.

Figure 3:
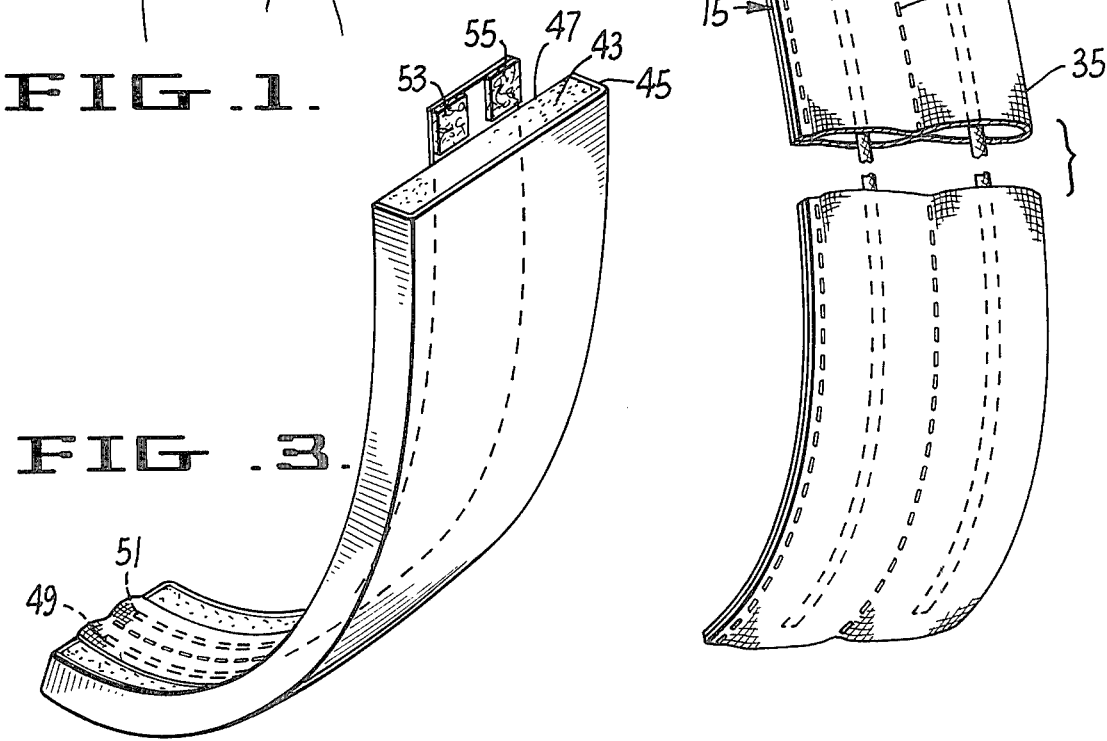
FIG. 3 is a perspective view of an alternate form of sensor unit.

In FIG. 3 another form of sensor unit is shown. In this embodiment of the device, a pad 43 of an absorptive material such as a diaper material is provided with an outer layer 45 of a thin, flexible plastic while the inner surface 47 is not covered. Wires 49 and 51 are exposed or thinly embedded in the open surface 47 of the diaper material. These wires are connected to the conductive Velcro ® pads 53 and 55 which mate with the Velcro ® pads 29 previously described.

Figure 4:
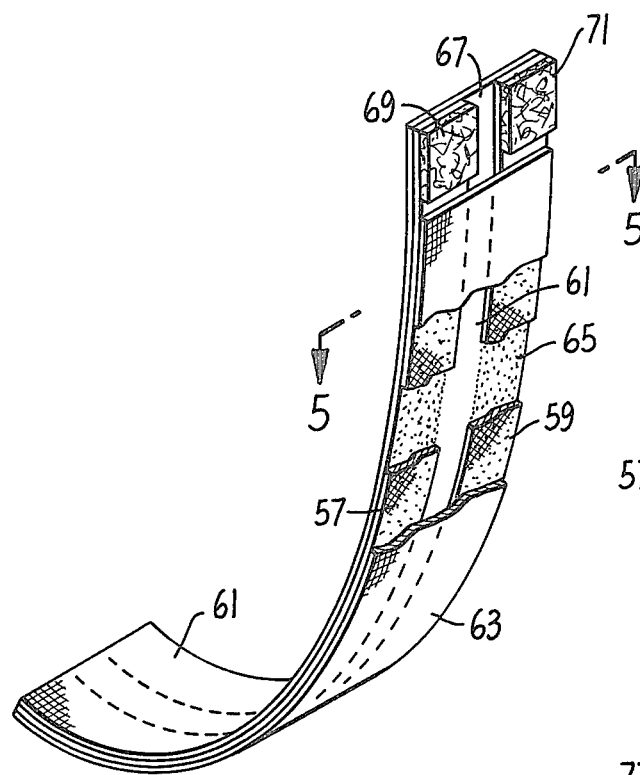
FIG. 4 is a perspective view of another type of sensor unit.
Figure 5:
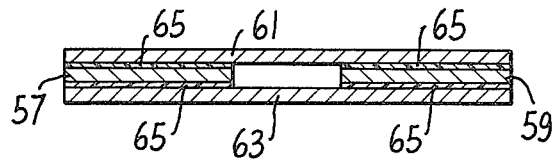
FIG. 5 is a section on the line 5—5 of FIG. 4.

FIGS. 4 and 5 show yet another embodiment of the sensor unit and in this embodiment a conductive polyvinyl cloth (such as that manufactured by the Herculite Company) is employed instead of the wires. Referring to FIGS. 4 and 5, two strips 57 and 59 of the conductive cloth are employed and these are held in spaced relationship between an upper layer 61 and a lower layer 63 of a cloth such as diaper cloth. The parts are held together by means of the adhesive layers 65 or can be sewed together with nonconductive thread. The outer layer 61 terminates short of the inner layer 63, leaving a portion of the inner layer exposed as at 67. Tabs of conductive Velcro ® 69 are attached to each of the inner layers of conductive cloth.

Figure 7:
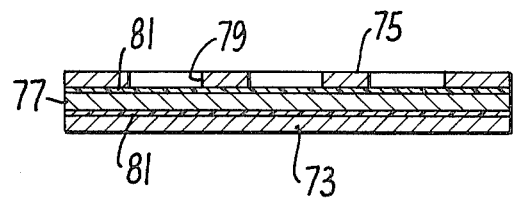
FIG. 7 is a section on the line 7—7 of FIG. 6.
Figure 6:
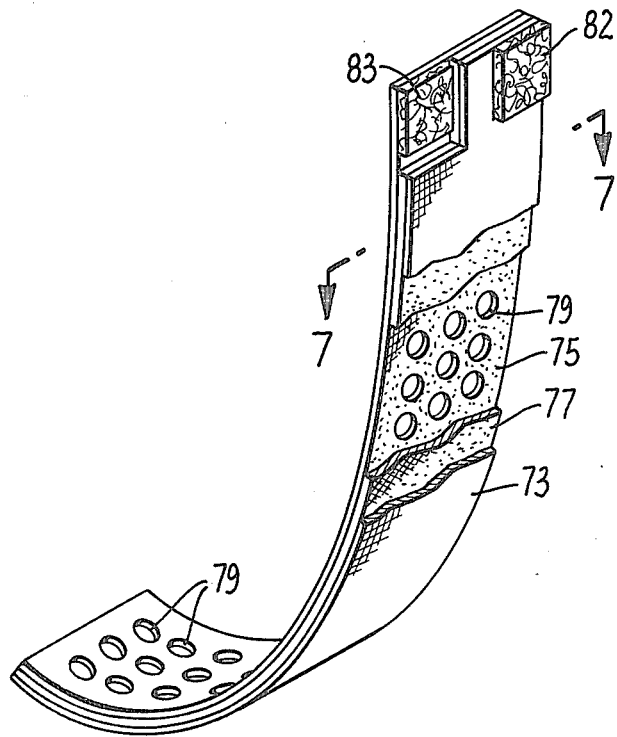
FIG. 6 is a perspective view of still another form of sensor unit.
Figure 8:
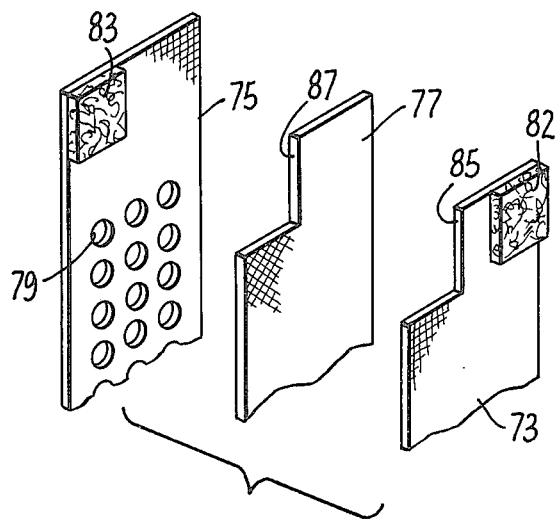
FIG. 8 is a partial exploded view of the structure shown in FIG. 6.
Figure 10:
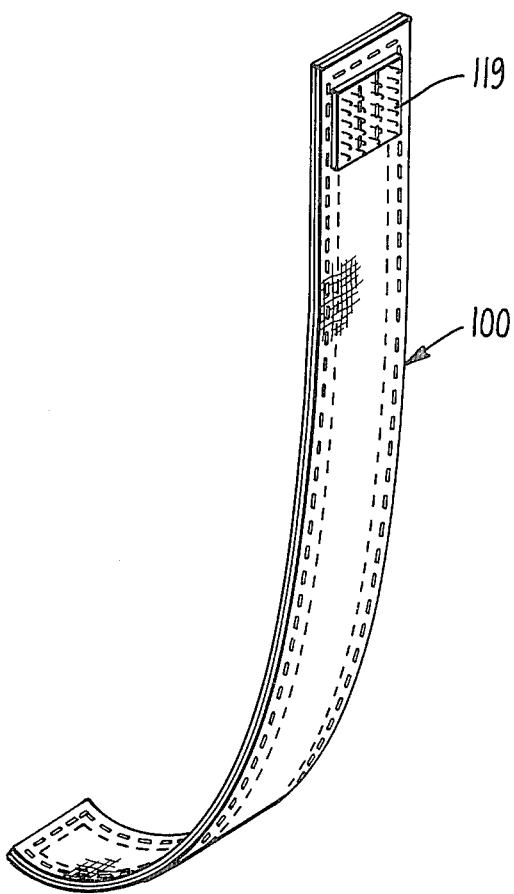
FIG. 10 is a perspective view of another sensor unit wherein layers of conductive cloth are placed back to back.
Figure 11:
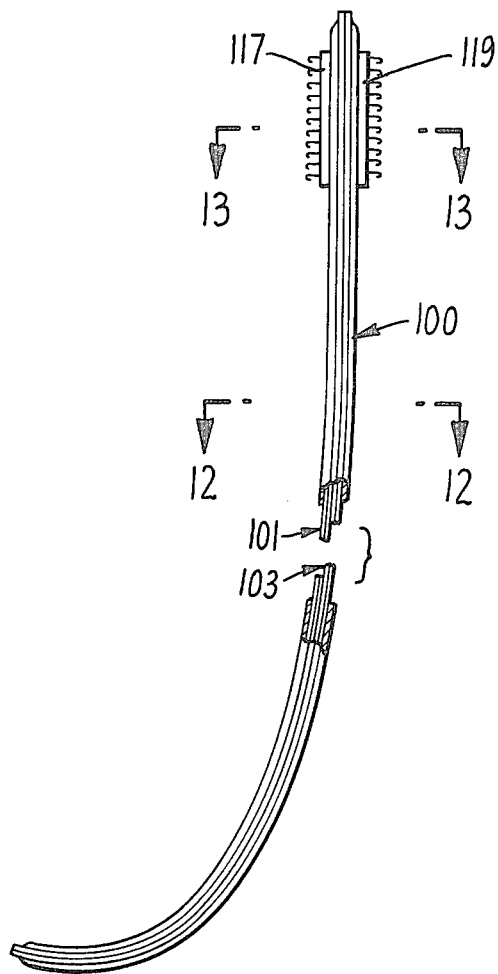
FIG. 11 is a side view, partially in section, of the structure shown in FIG. 10.
Figure 12:
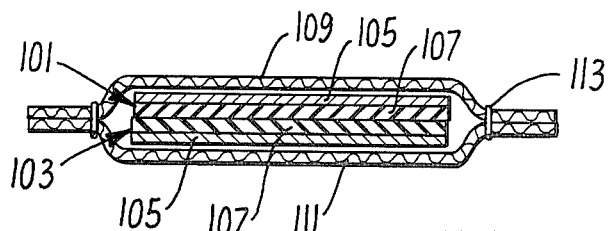
FIG. 12 is an enlarged section on the line 12—12 of FIG. 11.
Figure 13:
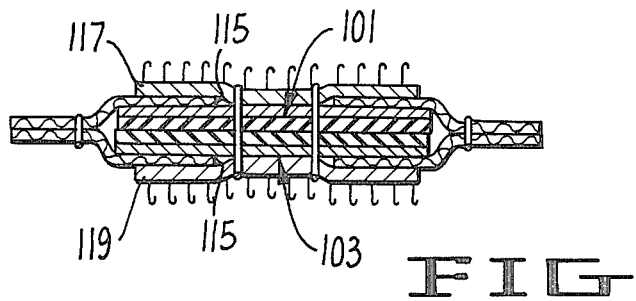
FIG. 13 is an enlarged section on the line 13—13 of FIG. 11.

Referring now to FIGS. 6–8, another embodiment of the invention is shown which also uses the conductive polyvinyl cloth. In this embodiment of the invention, the conductive strips instead of being arranged side-by-side are sandwiched together. Thus, there is provided an outer layer 73 and an inner layer 75 of conductive cloth separated by a layer 77 of ordinary cloth such as diaper material. The inner layer 75 has a plurality of perforations 79 therein to permit urine to migrate freely between the layers. The various layers are held together by means of a suitable adhesive 81 or sewn with thread. Conductive Velcro ® patches 82 and 83 are connected to the ends of the conductive cloth strips 73 and 75 respectively. The outer strip 73 is notched at 85 and the intermediate strip 75 notched at 87 so that the Velcro ® patch 83 will be exposed.

Figure 9:
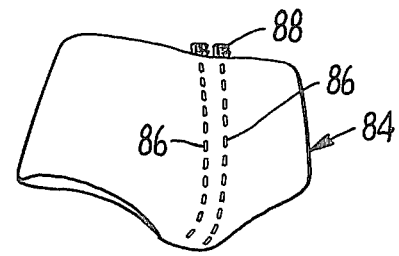
FIG. 9 is a perspective view of a sensor wherein the sensing element is formed as part of a garment.

Although it is preferred that the sensor be built as a unit and placed in the lower half of a sleeping garment, the sensor can be built into the garment itself as is shown in FIG. 9. In this case, that portion of the garment between the two electrodes would become conductive when wet, thereby completing the circuit and sounding the alarm. Here pants 84 have wires 86 incorporated therein which lead to the Velcro ® tabs 88. Of course, strips of conductive polyvinyl cloth could be employed instead of the wires.

Another form of sensor is shown in FIGS. 10–13. In this form of sensor unit, the conductive polyvinyl cloth, previously mentioned, is utilized and advantage is taken of the fact that the cloth is conductive on only one side and the opposite side of the cloth is an insulator. Thus, it is possible to provide a very simple sensor wherein two strips of the conductive cloth are employed with the nonconductive surfaces in contact with each other. This is enclosed in a simple cotton envelope of diaper material with the conductive Velcro ® contacts on opposite sides. This unit is very sensitive since a conductive path is established around the edges of the sensor through the diaper cloth which forms the envelope.

Referring to FIGS. 10–13, the sensor includes a first strip 101 of conductive polyvinyl cloth and a second strip 103. The polyvinyl cloth has a conductive layer 105 and a nonconductive layer 107. The two strips can be placed against each other since the insulating sides are in contact with each other, as shown. The two strips are enclosed in a sheath formed of the layers 109 and 111, which can be of ordinary cotton diaper material formed into an envelope by the side stitching 113. At one end of the strips a small hole 115 is made into each strip of cotton cloth and conductive Velcro ® patches 117 and 119 are applied on each side so that the conductive Velcro ® patches are in contact with the respective conductive sides of the polyvinyl cloth.

This form of sensor is very simple and inexpensive to make and the stitching can pass through the conductive strips of polyvinyl cloth if desired. Further, it has been found that the stitching can go right through the Velcro ® pads if the pads are of the hook type. The sensors shown in this embodiment of the invention are very inexpensive to prepare since they can be made in endless strips, sliced into segments, and the Velcro ® applied thereto before or after severing the strips into segments. The sensors can be pressed onto a sleeping garment with a hot iron utilizing known binding cloths. They can be easily laundered and will return to their nonconductive form upon drying. With this form of sensor the connectors to the sounder must face each other, rather than being side-by-side as is shown in FIG. 2.

Figure 14:
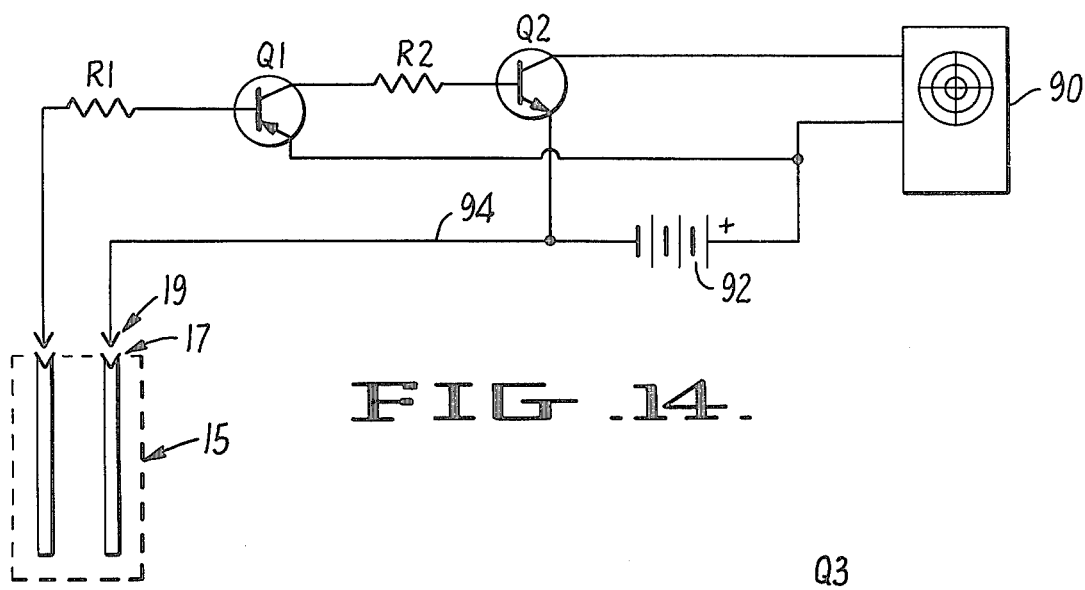
FIG. 14 is a schematic diagram of a simple form of electrical circuit.

Various alarm devices can be used with the sensors of the present invention. In FIG. 14 a simple indicator is shown utilizing a miniature alarm buzzer 90. The positive terminal of battery 92 is connected to the alarm and to an emitter of transistor Q1. The negative terminal of the battery is connected through line 94 to one pole of the sensor and to the emitter of transistor Q2. The opposite terminal of the sensor is connected to the base of transistor Q1 through resistor R1 and the collector of Q1 is connected through resistor R2 to the base of transistor Q2. It is obvious that when there is no conductivity between the two probes of the sensor, no current will flow from the battery to the buzzer since transistor Q2 is cut off. Now if a conductive path is established between the probes of the sensor as by urine, a negative current flows through resistor R1 to the base of transistor Q1 causing Q1 to conduct. When Q1 conducts, the base of transistor Q2 conducts turning on the buzzer 90. If the circuit of a sensor is broken such as by disconnecting the sensor, the buzzing will stop. Thus, the child upon hearing the buzzer can shut the buzzer off by breaking a connection between the upper and lower portions of the garment.

Figure 15:
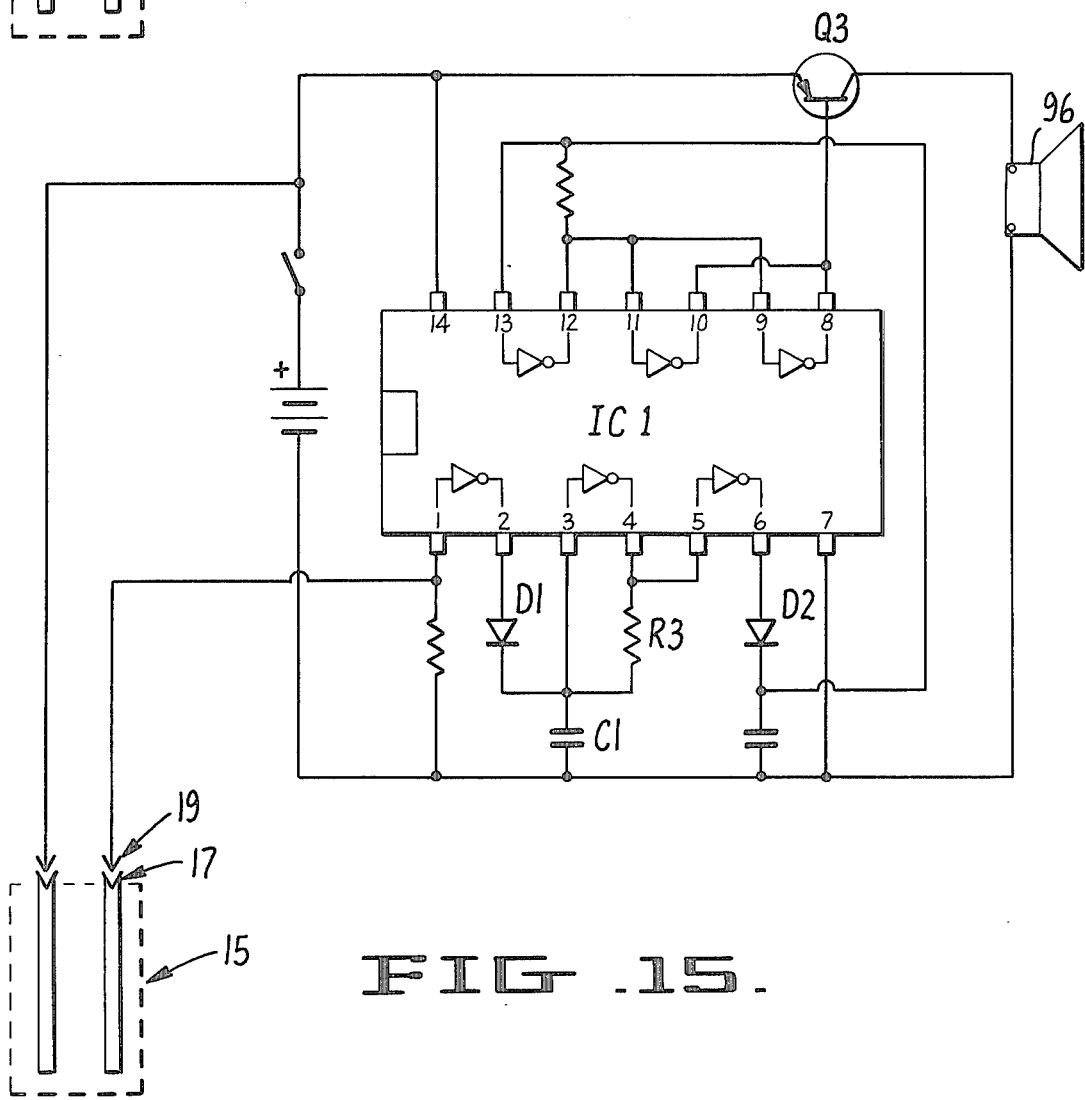
FIG. 15 is a schematic diagram of another form of warning circuit.

In FIG. 15 a preferred circuit is shown utilizing a hexinverter chip such as 74C14 or MC14584 which is designated IC 1 in the drawing. In this circuit, if moisture is present between the electrodes of the sensor 15, pin 1 of IC 1 will go positive causing pin 2 to go low, releasing the clamp diode D1. This permits the Schmitt oscillator formed between pins 3 and 4 to produce a square wave output at a frequency of about 1 Hz. This frequency is controlled by C1 and R3. This is buffered by the trigger between pins 5 and 6 alternately clamping and releasing D2. This permits the oscillator formed between pins 12 and 13 to oscillate at approximately 1 kHz at halfsecond intervals. The parallel connected Schmitt triggers 11 and 10 and 9 and 8 buffer this 50% duty cycle and drive Q3 which in turn drives the speaker 96 to produce an audible tone at about 1 kHz which turns on and off each half second. When the connections to the probe are broken, the circuit turns off. This circuit is preferred because of the on-off nature of the tone which is much more reliable in awakening the sleeper.

Referring now specifically to FIGS. 16 through 18, wherein a preferred embodiment of the sensor and connector are shown, the device consists of a sounder, generally designated 100, connected by means of flat strips generally designed 102, to a "plug and jack" unit 104 to the sensor 106. The sounder 100 can be of any type, such as those well-known to those skilled in the art, including those previously described, which have wires 108 and 110, wherein the sounder will be activated when a circuit is established between the two wires. In this embodiment of the invention, the leads consist of two strips 112 and 114 of conductive vinyl cloth, as previously described. These are enclosed in two sheaths 116 and 118 of a soft yet strong fabric such as dacron. At the upper end, a small piece of conductive rubber 120 is attached by means of a small staple 122 which lies along the conductive side of the vinyl cloth. A similar connection is made between the strip 114 and wire 108. A small strip of adhesive tape 124 is placed over the connection to provide strength and insulation.

At the opposite end of the strips are placed small pieces of conductive Velcro ® 126 and 128. These mate with strips of conductive Velcro ® 130 and 132 which are connected to the conductive strips of the sensor strips 134 and 136. In the embodiment illustrated the connector is provided with loop Velcro ® and the sensor is provided with hook Velcro ®, but obviously this situation could be reversed. The sensor 106 is as previously described and consists of two strips of polyvinyl cloth, each of which has a nonconductive side 138 and 140 and the conductive sides, previously described, 134 and 136. These are held inside of a cloth sheath 142 as previously described.

It will be understood that the embodiment shown in 16–18 are the best known mode of practicing the invention since both the sensor proper and the conductors leading from the sensor to the sounder are made of flexible polyvinyl strips. Since the conductors are enclosed in strong cloth, they are not subject to breakage as ordinary wire conductors might be. Further, since they are very soft and flexible, they do not interfere with the comfort of the sleeper.

The device of the present invention is ordinarily not provided with an off-on switch so that it is desirable to provide some means of preventing accidental sounding of the device when it is not in use. For this purpose, it is convenient to provide a small pad 144 of Velcro ® spaced some distance from the ends 126 and 128 and to provide a small pad 146 of the opposite type of Velcro ® on the outer surface of the corresponding conductor. Thus, when the device is not in use, 144 and 146 can be pressed together, obviating any danger of false triggering by contact between 126 and 128.

It is believed apparent from the foregoing that we have provided a simple sensor for an anti-bed-wetting device which is very sensitive so that it will be activated by only a few drops of urine. Since the device is actuated by the first few drops of urine, soiling of the bed and clothing is largely prevented. Rapid activation of the device by placing a wetness sensor in the sleepwear is also thought to aid in conditioning the subject to learn to wake up prior to the involuntary release of urine. Further, the preferred form of lead from the sensor to the sounder is strong yet comfortable for the wearer.

We claim:

1. In an anti-bed-wetting device consisting of an electrical sounder adapted to be triggered by the closing of a pair of contacts, a sensor, and an electrically conducting means between said sounder and said sensor, the improvement comprising a sensor comprising two relatively long, narrow strips of a conductive fabric wherein said fabric has a conductive side and a nonconductive side, said strips being of substantially the same size and configuration and being placed in back-to-back relationship with the nonconductive sides of each sheet in contact with the other and a sheet of fabric or cloth enclosing said strips and at one end of said sensor two small patches of electrically conductive Velcro ® in back-to-back relationship, with the attaching sides of the Velcro ® facing outwardly, one of said Velcro ® patches being in electrical contact with each of said strips.

2. The device of claim 1 wherein said electrically conductive means comprises a pair of face-to-face conductive fabric strips each of which has a patch of inwardly facing conductive Velcro ® at the terminal ends thereof, said strips being enclosed in a fabric sheath and said Velcro ® strips adapted to mate with said corresponding patches on said sensor.

* * * * *